United States Patent
Paul et al.

(10) Patent No.: US 8,685,218 B2
(45) Date of Patent: *Apr. 1, 2014

(54) PRECISION FLOW CONTROL SYSTEM

(75) Inventors: Phillip H. Paul, Livermore, CA (US);
Jason E. Rehm, Alameda, CA (US);
Don W. Arnold, Livermore, CA (US)

(73) Assignee: AB Sciex LLC, Framingham, MA (US)

( * ) Notice: Subject to any disclaimer, the term of this patent is extended or adjusted under 35 U.S.C. 154(b) by 390 days.

This patent is subject to a terminal disclaimer.

(21) Appl. No.: 13/046,496

(22) Filed: Mar. 11, 2011

(65) Prior Publication Data

US 2011/0186157 A1    Aug. 4, 2011

Related U.S. Application Data

(60) Continuation of application No. 12/334,375, filed on Dec. 12, 2008, now Pat. No. 7,927,477, which is a division of application No. 10/246,284, filed on Sep. 17, 2002, now Pat. No. 7,465,382.

(51) Int. Cl.
*G05B 24/04* (2006.01)
(52) U.S. Cl.
USPC .......................... 204/600; 422/105; 422/110
(58) Field of Classification Search
USPC .................................. 204/600; 422/105, 110
See application file for complete search history.

(56) References Cited

U.S. PATENT DOCUMENTS

| | | | |
|---|---|---|---|
| 2,615,940 A | 10/1952 | Williams | |
| 2,644,900 A | 7/1953 | Hardway, Jr. | |
| 2,644,902 A | 7/1953 | Hardway, Jr. | |
| 2,661,430 A | 12/1953 | Hardway, Jr. | |
| 2,995,714 A | 8/1961 | Hannah | |
| 3,143,691 A | 8/1964 | Hurd | |
| 3,209,255 A | 9/1965 | Estes et al. | |
| 3,427,978 A | 2/1969 | Hanneman et al. | |
| 3,544,237 A | 12/1970 | Walz | |
| 3,682,239 A | 8/1972 | Abu-Romia | |
| 3,917,531 A | 11/1975 | Magnussen | |
| 3,921,041 A | 11/1975 | Stockman | |

(Continued)

FOREIGN PATENT DOCUMENTS

| CN | 2303885 | 3/1997 |
|---|---|---|
| CN | 2286429 | 7/1998 |

(Continued)

OTHER PUBLICATIONS

Office Action for U.S. Appl. No. 10/246,284, mailed Sep. 30, 2005, 6 pages.

(Continued)

*Primary Examiner* — Arun S Phasge
(74) *Attorney, Agent, or Firm* — Bella Fishman

(57) ABSTRACT

A precision flow controller is capable of providing a flow rate less than 100 microliters/minute and varying the flow rate in a prescribed manner that is both predictable and reproducible where the accuracy and precision of the flowrate is less than 5% of the flow rate. A plurality of variable pressure fluid supplies pump fluid through a single outlet. Flowmeters measure the flow rates and a controller compares the flow rates to desired flowrates and, if necessary, adjusts the plurality of variable pressure fluid supplies so that the variable pressure fluid supplies pump fluid at the desired flow rate. The variable pressure fluid supplies can be pneumatically driven.

16 Claims, 10 Drawing Sheets

(56) References Cited

U.S. PATENT DOCUMENTS

| | | | |
|---|---|---|---|
| 3,923,426 A | 12/1975 | Theeuwes | |
| 4,347,131 A | 8/1982 | Brownlee | |
| 4,638,444 A | 1/1987 | Laragione et al. | |
| 4,681,678 A | 7/1987 | Leaseburge et al. | |
| 4,684,465 A | 8/1987 | Leaseburge et al. | |
| 4,767,279 A | 8/1988 | Dourdeville et al. | |
| 4,810,392 A | 3/1989 | Fulton et al. | |
| 4,921,041 A | 5/1990 | Akachi | |
| 5,032,264 A | 7/1991 | Geiger | |
| 5,040,126 A | 8/1991 | Allington | |
| 5,219,020 A | 6/1993 | Akachi | |
| 5,249,929 A | 10/1993 | Miller et al. | |
| 5,302,264 A | 4/1994 | Welch et al. | |
| 5,312,233 A | 5/1994 | Tanny et al. | |
| 5,418,079 A | 5/1995 | Diethelm | |
| 5,429,728 A | 7/1995 | Gordon | |
| RE35,010 E | 8/1995 | Price | |
| 5,482,608 A | 1/1996 | Keely et al. | |
| 5,573,651 A | 11/1996 | Dasgupta et al. | |
| 5,630,706 A | 5/1997 | Yang | |
| 5,664,938 A | 9/1997 | Yang | |
| 5,670,707 A | 9/1997 | Fennell et al. | |
| 5,777,213 A | 7/1998 | Tsukazaki et al. | |
| 5,797,719 A | 8/1998 | James et al. | |
| 5,814,742 A | 9/1998 | Vissers et al. | |
| 5,858,193 A | 1/1999 | Zanzucchi et al. | |
| 5,888,050 A | 3/1999 | Fitzgerald et al. | |
| 5,915,401 A | 6/1999 | Menard et al. | |
| 5,942,093 A | 8/1999 | Rakestraw et al. | |
| 5,961,800 A | 10/1999 | McBride et al. | |
| 5,997,746 A | 12/1999 | Valaskovic | |
| 6,004,443 A | 12/1999 | Rhodes et al. | |
| 6,012,902 A | 1/2000 | Parce | |
| 6,013,164 A | 1/2000 | Paul et al. | |
| 6,019,882 A | 2/2000 | Paul et al. | |
| 6,045,933 A | 4/2000 | Okamoto | |
| 6,068,243 A | 5/2000 | Hoggan | |
| 6,068,767 A | 5/2000 | Garguilo et al. | |
| 6,086,243 A | 7/2000 | Paul et al. | |
| 6,106,685 A | 8/2000 | McBride et al. | |
| 6,139,734 A | 10/2000 | Settlage et al. | |
| 6,167,910 B1 | 1/2001 | Chow | |
| 6,221,332 B1 | 4/2001 | Thumm et al. | |
| 6,224,728 B1 | 5/2001 | Oborny et al. | |
| 6,255,551 B1 | 7/2001 | Shapiro et al. | |
| 6,277,257 B1 | 8/2001 | Paul et al. | |
| 6,280,967 B1 | 8/2001 | Ransom et al. | |
| 6,287,440 B1 | 9/2001 | Arnold et al. | |
| 6,289,914 B1 | 9/2001 | Tommasi | |
| 6,290,909 B1 | 9/2001 | Paul et al. | |
| 6,299,767 B1 | 10/2001 | Dourdeville | |
| 6,315,905 B1 | 11/2001 | Settlage et al. | |
| 6,319,410 B1 | 11/2001 | Allington et al. | |
| 6,386,050 B1 | 5/2002 | Yin et al. | |
| 6,402,946 B1 | 6/2002 | Spraul et al. | |
| 6,404,193 B1 | 6/2002 | Dourdeville | |
| 6,406,605 B1 | 6/2002 | Moles | |
| 6,416,642 B1 | 7/2002 | Alajoki et al. | |
| 6,428,666 B1 | 8/2002 | Singh et al. | |
| 6,460,420 B1 | 10/2002 | Paul et al. | |
| 6,477,410 B1 | 11/2002 | Henley et al. | |
| 6,616,823 B2 | 9/2003 | Kopf-Sill | |
| 6,619,311 B2 | 9/2003 | O'Connor et al. | |
| 6,719,535 B2 | 4/2004 | Rakestraw et al. | |
| 6,766,817 B2 | 7/2004 | Da Silva | |
| 7,465,382 B2 * | 12/2008 | Paul et al. | 204/600 |
| 7,927,477 B2 * | 4/2011 | Paul et al. | 204/600 |
| 2001/0008212 A1 | 7/2001 | Shepodd et al. | |
| 2001/0020589 A1 | 9/2001 | Kopf-Sill | |
| 2002/0017484 A1 | 2/2002 | Dourdeville | |
| 2002/0022802 A1 | 2/2002 | Simpson | |
| 2002/0070116 A1 | 6/2002 | Ohkawa | |
| 2002/0072126 A1 | 6/2002 | Chervet et al. | |
| 2002/0076598 A1 | 6/2002 | Bostaph et al. | |
| 2002/0125134 A1 | 9/2002 | Santiago et al. | |
| 2002/0189947 A1 | 12/2002 | Paul et al. | |
| 2002/0195344 A1 | 12/2002 | Neyer et al. | |
| 2003/0052007 A1 | 3/2003 | Paul et al. | |
| 2003/0138678 A1 | 7/2003 | Preidel | |
| 2003/0190514 A1 | 10/2003 | Okada et al. | |
| 2003/0215686 A1 | 11/2003 | Defilippis et al. | |
| 2004/0011648 A1 | 1/2004 | Paul et al. | |
| 2004/0107996 A1 | 6/2004 | Crocker et al. | |
| 2007/0000784 A1 | 1/2007 | Paul et al. | |

FOREIGN PATENT DOCUMENTS

| | | |
|---|---|---|
| DE | 19625648 | 1/1997 |
| EP | 0183950 | 6/1986 |
| JP | 50116893 | 12/1975 |
| JP | 6197567 | 5/1986 |
| JP | 61237717 | 10/1986 |
| JP | 168503 | 2/1989 |
| JP | 618964 | 3/1994 |
| JP | 07072934 | 3/1995 |
| JP | 09281077 | 10/1997 |
| WO | 8502225 | 5/1985 |
| WO | WO9639252 | 12/1996 |
| WO | WO9916162 | 4/1999 |
| WO | WO9967639 | 12/1999 |
| WO | WO0004832 | 2/2000 |
| WO | WO0016937 | 3/2000 |
| WO | WO0043766 | 7/2000 |
| WO | WO0055502 | 9/2000 |
| WO | WO0065337 | 11/2000 |
| WO | WO0079131 | 12/2000 |
| WO | WO02068821 | 9/2002 |
| WO | WO2004007080 | 1/2004 |

OTHER PUBLICATIONS

Office Action for European Patent Application No. 03 759 457.9, dated Nov. 8, 2005, 4 pages.
Office Action for U.S. Appl. No. 10/246,284, mailed Oct. 4, 2006, 5 pages.
Office Action for U.S. Appl. No. 10/246,284, mailed Jan. 27, 2006, 6 pages.
Office Action for European Patent Application No. 02 739 909.6, dated Apr. 18, 2007, 4 pages.
Office Action for U.S. Appl. No. 10/246,284, dated Jul. 16, 2007, 6 pages.
Office Action for Indian Patent Application No. 51/CHENP/2004, mailed Jul. 16, 2007, 2 pages.
Office Action for European Patent Application No. 03 759 457.9, dated Feb. 7, 2008, 10 pages.
Office Action for U.S. Appl. No. 10/246,284, dated Apr. 18, 2008, 21 pages.
Notice of Allowance for U.S. Appl. No. 10/245,284, dated Aug. 22, 2008, 7 pages.
Office Action for U.S. Appl. No. 11/200,369, dated Apr. 2, 2009, 15 pages.
Notice of Rejection for Japanese Patent Application No. 2004-538456, dated May 26, 2009, 3 pages.
Office Action for European Patent Application 03759457.9, dated Nov. 8, 2005, 4 pages.
Office Action for European Patent Application 03759457.9, dated Feb. 7, 2008, 10 pages.
Supplementary European Search Report for European Patent Application 02739909.6, dated Jul. 5, 2005, 3 pages.
Office Action for European Patent Application 02739909.6, dated Feb. 2, 2006, 3 pages.
Office Action for European Patent Application 027399-9.6 dated Apr. 18, 2007, 4 pages.
Office Action for U.S. Appl. No. 09/942,884 mailed on Apr. 22, 2004, 5 pages.
Office Action for U.S. Appl. No. 09/942,884 mailed on Aug. 12, 2004, 9 pages.
Office Action for U.S. Appl. No. 09/942,884 mailed on Mar. 9, 2005, 7 pages.

(56) References Cited

OTHER PUBLICATIONS

Advisory Action for U.S. Appl. No. 09/942,884, mailed on May 24, 2005, 3 pages.
Office Action for U.S. Appl. No. 10/155,474 mailed on Jul. 13, 2005, 5 pages.
Office Action for U.S. Appl. No. 10/155,474 mailed on Nov. 4, 2005, 6 pages.
Office Action for U.S. Appl. No. 10/155,474 mailed on Jul. 18, 2006, 6 pages.
International Search Report for PCT App. No. PCT/US02/19121, mailed Jan. 3, 2003, 4 pages.
International Preliminary Examination Report for PCT App. No. PCT/US02/19121, mailed Mar. 7, 2003, 4 pages.
Office Action for U.S. Appl. No. 10/480,619, mailed Oct. 9, 2007, 6 pages.
International Search Report, for PCT Application No. PCT/US03/30008, mailed Mar. 4, 2004, 4 pages.
Notice of Rejection for Japanese Patent Application No. 2003-504171, dated May 7, 2008, 3 pages. (unofficial English translation).
Low Flow High-Performance Liquid Chromatography Solvent Delivery System Designed for Tandem Capillary Liquid Chromatography-Mass Spectrometry, M.T. Davis, D.C. Stahl, and T.D. Lee; J. Am Soc, Mass Spectrom 1995, 6, 571-577.
Data-Controlled Automation of Liquid Chromatography/Tandem Mass Spectrometry Analysis of Peptide Mixtures, Douglas C. Stahl, Kristine M. Swiderek, Michael T. Davis, and Terry D. Lee; J. Am. Soc. Mass Spectrom 1996, 7, 532-540.
Variable Flow Liquid Chromatography-Tandem Mass Spectrometry and the Comprehensive Analysis of Complex Protein Digest Mixtures, Michael T. Davis and Terry D. Lee; J. Am. Soc. Mass Spectrom 1997, 8, 1059-1069.
Subfemtomole MS and MS/MS Peptide Sequence Analysis Using Nano-HPLC Micro-ESI Fourier Transform Ion Cyclotron Resonance Mass Spectrometry, Susan E. Martin, Jeffrey Shabanowitz, Donald F. Hung, and Jarrod A. Marto, Anal. Chem. 2000, 72, 4266-4274.
Nano-Scale Variable Flow Chromatography for High Sensitivity Proteome Studies, James Langridge, Allan Millar, Chris Hughes, Hans Vissers, Tad Dourdeville and Philip Young, Present at Combio, Canberra, Australia, Sep. 30-Oct. 4, 2001.
A Novel Interface for Variable Flow Nanoscale LC/MS/MS for Improved Proteome Coverage, Johannes P.C. Vissers; R. Kevin Blackburn and M. Arthur Moseley, J. Am. Soc. Mass Spectrom 2002, 13 760-771.
High Sensitivity Phosphoprotein Analysis Using a Combination of Variable Flow Chromatography and Precursor Ion Discovery on a Q-TOF Mass Spectrometer, James Langridge, Alistair Wallace, Alan Millar, Chris Hughes, Hans Vissers, Tad Dourdeville and Phillip Young, Presented at 19th Montreux Symposium, Montreux, Switzerland, Nov. 6-8, 2002.
Adamson, A.W. et al., Physical Chemistry of Surfaces, pp. 185-187 (Wiley, NY 1997).
Desiderio et al., Electrophoresis, 20:525-528 (1999).
Gan, W. et al. Talanta 51:667-675 (2000).
Kobatake, Y. et al., J. Chem. Phys. 40(8):2212-2218 (Apr. 1964).
Kobatake, Y. et a)., J. Chem. Phys. 40(8):2219-2222 (Apr. 1964).
Morrison, F.A. et al., J. Chem. Phys. 43:2111-2115 (1965).
Paul, P.H. et al., Micro Total Analysis Systems, pp. 49-52 (1998).
Paul, P.H. et al., Micro Total Analysis Systems, pp. 583-590 (2000).
Rastogi, R.P., J. Scient. Ind. Res., (28):284-292 (Aug. 1969).
Schmid, G. J. Membrane Sci. 150:159-170 (1998).
Schmid, G. et al., J. Membrane Sci. 150:197-209 (1998).
Zeng, S. et al., Sensors and Actuators, B 79:107-114 (2001).
European Search Report for EP 02 73 9909 dated Jul. 5, 2005.
Ananthakrishnan, V. et al., "Laminar Dispersion in Capillaries: Part I. Mathematical Analysis," A.I.Ch.E. Journal, 11 (6):1063-1072 (Nov. 1965).
Yazawa, T., "Present Status and Future Potential of Preparation of Porous Glass and its Application," Key Engineering Materials, 115:125-146 (1995).
"Capillary or standard LC-for the greatest flexibility in your laboratory," Agilent Technologies: Agilent 1100 Series Capillary LC System, A one-vendor solution for highest sensitivity and robustness.
Aris, R., "On the dispersion of a solute in a fluid flowing through a tube," Oxidation of organic sulphides. VI, Proc. Rev. Soc. (London), 235A:67-77.
Burgreen, D. et al., "Electrokinetic Flow in Ultrafine Capillary Slits," The Journal of Physical Chemistry, 68:5 1084-1091 (May 1964).
Carvalho, R.T. et al. "Slow-flow measurements and fluid dynamics analysis using the Fresnel drag effect," Applied Optics, vol. 33, No. 25 (Sep. 1, 1994).
Chatwin, P.C. et al., "The effect of aspect ratio on longitudinal diffusivity in rectangular channels," J. Fluid Mech., 120:347-358 (1982).
Doshl, Mahendra R. et al., "Three Dimensional Laminar Dispersion in Open and Closed Rectangular Conduits," Chemical Engineering Science, 33:795-804 (1978).
Drott, J. et al., "Porous silicon as the carrier matrix in microstructured enzyme reactors yielding high enzyme activities," J. Micromech. Microeng. 7:14-23 (1977).
Enoksson, Peter et al., "A Silicon Resonant Sensor Structure for Coriolis Mass-Flow Measurements," Journal of Microelectromechanical Systems, vol. 6, No. 2 (Jun. 1997).
Jessensky O. et al., "Self-Organized Formation of Hexagonal Pore Structure in Anodic Alumina," J. Electrochem. Soc. 145(11):3735-3740 (Nov. 1998).
Johnson, David Linton et al., "New Pore-Size Parameter Characterizing Transport in Porous Media," Physical Review Letters, 57(20):2554-2567 (Nov. 17, 1986).
Johnson, David Linton et al., "Theory of dynamic permeability and tortouosity in fluid-saturated porous media," J. Fluid Mech. 176:379-402 (1987).
Johnson, David Linton et al., "Dependence of the conductivity of a porous medium on electrolyte conductivity," Physical Review Letters, 37(7): 3502-3510 (Mar. 1, 1988).
LeBlanc, Jacques C., "The Stableflow Pump—a low-noise and drift-free pump for high performance liquid chromatography," Rev. Sci. Instrum. 62(6), 1642-1646 (Jun. 1991).
Ma, Ying et al., "A Review of zeo-lite porous materials," Microporous and Mesoporous Materials, 37:243-242 (2000).
McNair, H.M., "High Pressure Liquid Chromatography Equipment-II," Journal of Chromatographic Science (Aug. 1974).
Nakanishi, Kazuki et al., "Phase separation in silica sol-gel system containing polyacrylic acid, I. Gel formation behavior and effect of solvent composition," Journal of Crystalline Solids, 139:1-13 (1992).
Peters, Eric C. et al., "Molded Rigid Polymer Monoliths as Separation Media for Capillary Electrochromatography," Anal. Chem., 69:3646-3649 (1997).
Philipse, Albert P., Solid opaline packings of colloidal silica spheres, Journal of Materials Science Letters, 8:1371-1373 (1989).
Rice, C.L., et al., "Electrokinetic Flow in a Narrow Cylindrical Capillary," The Journal of Physical Chemistry, 69 (11):4017-4023 (Nov. 1966).
Rosen, Milton J., 2. Adsorption of Surface-Active Agents at Interfaces: The Electrical Double Layer, Surfactants and Interfacial Phenomena, Second Ed., John Wiley & Sons.
Taylor, Geoffrey, Dispersion of soluble matter in solvent flowing slowly through a tube, Proc. Roy. Soc. (London) 21:186-203.
Vissers, Johannes P.C., "Recent developments in microcolumn liquid chromatography," Journal of Chromatography A, 856, 117-143 (1999).
Weston, Andrea at al., "Chapter 3 Instrumentation for High-Performance Liquid Chromatography," HPLC and CE, Principles and Practice, pp. 82-85, Academic Press.
Wijnhoven, Judith et al., "Preparation of Photonic Crystals Made of Air Spheres in Titania," Science, 281:802-804 (Aug. 7, 1998).

* cited by examiner

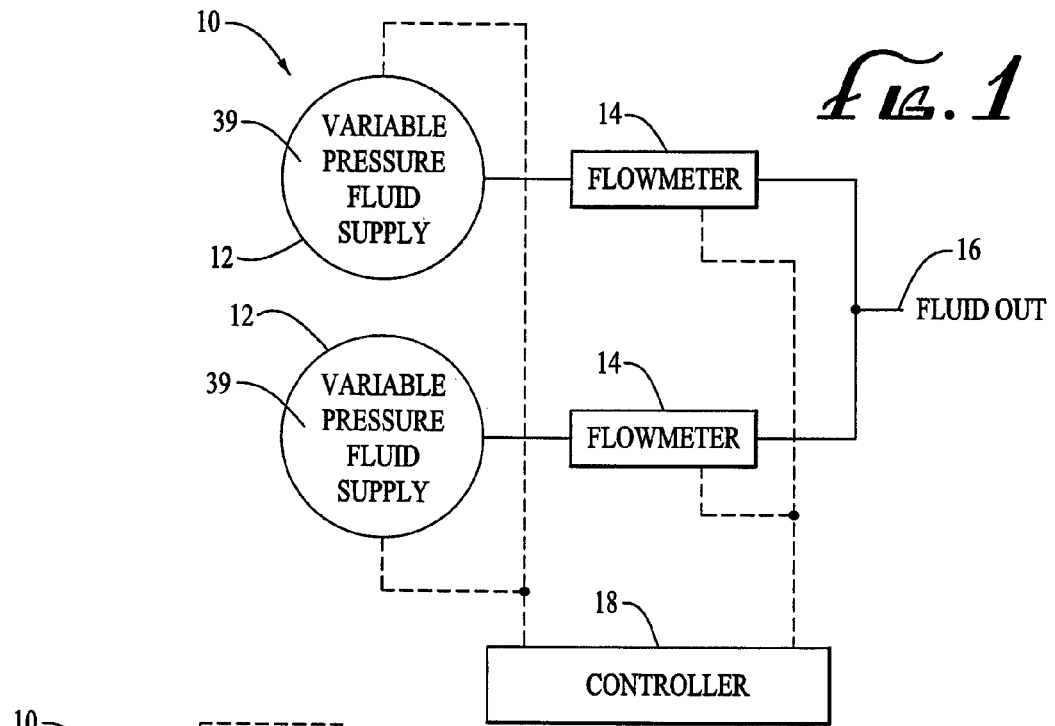
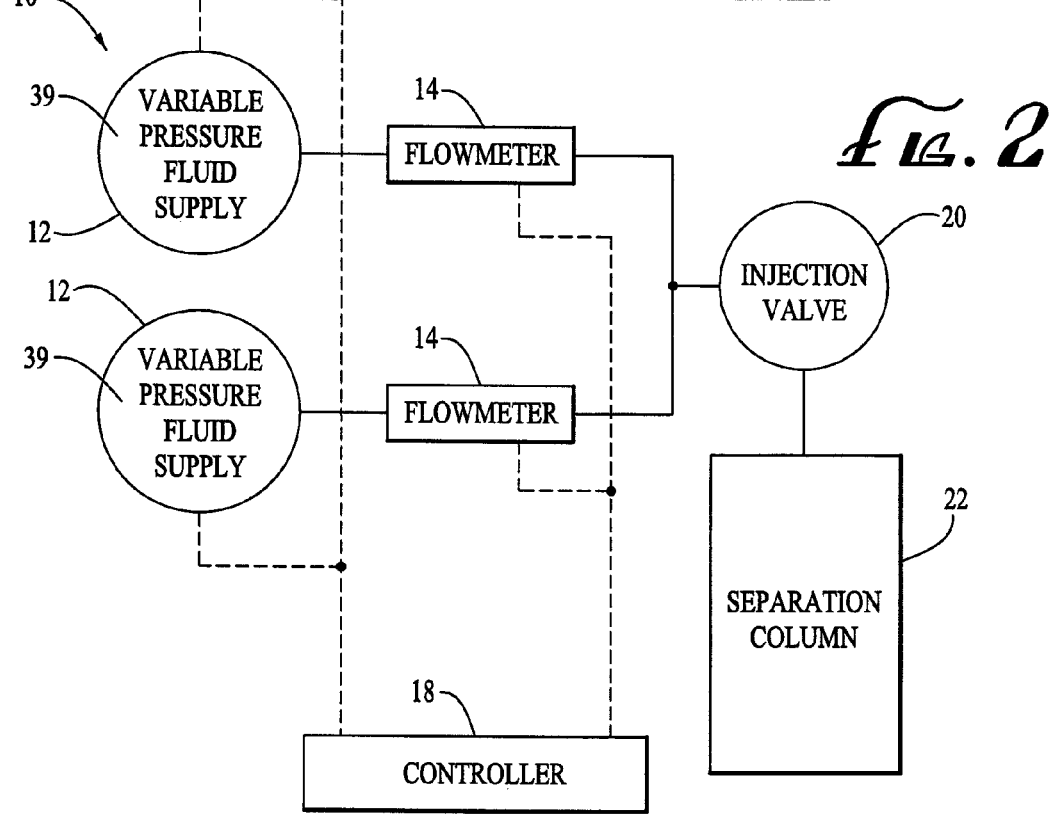

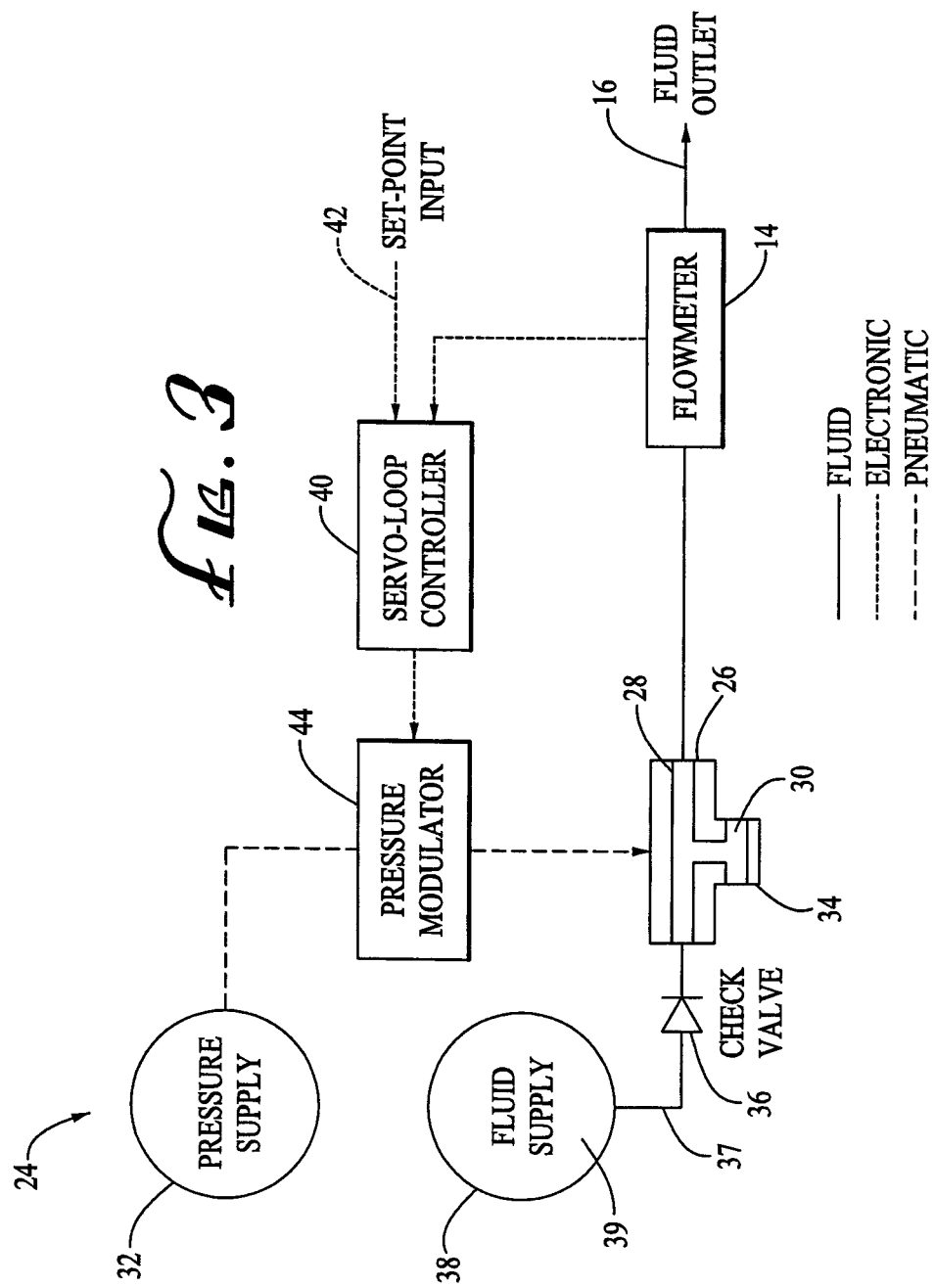

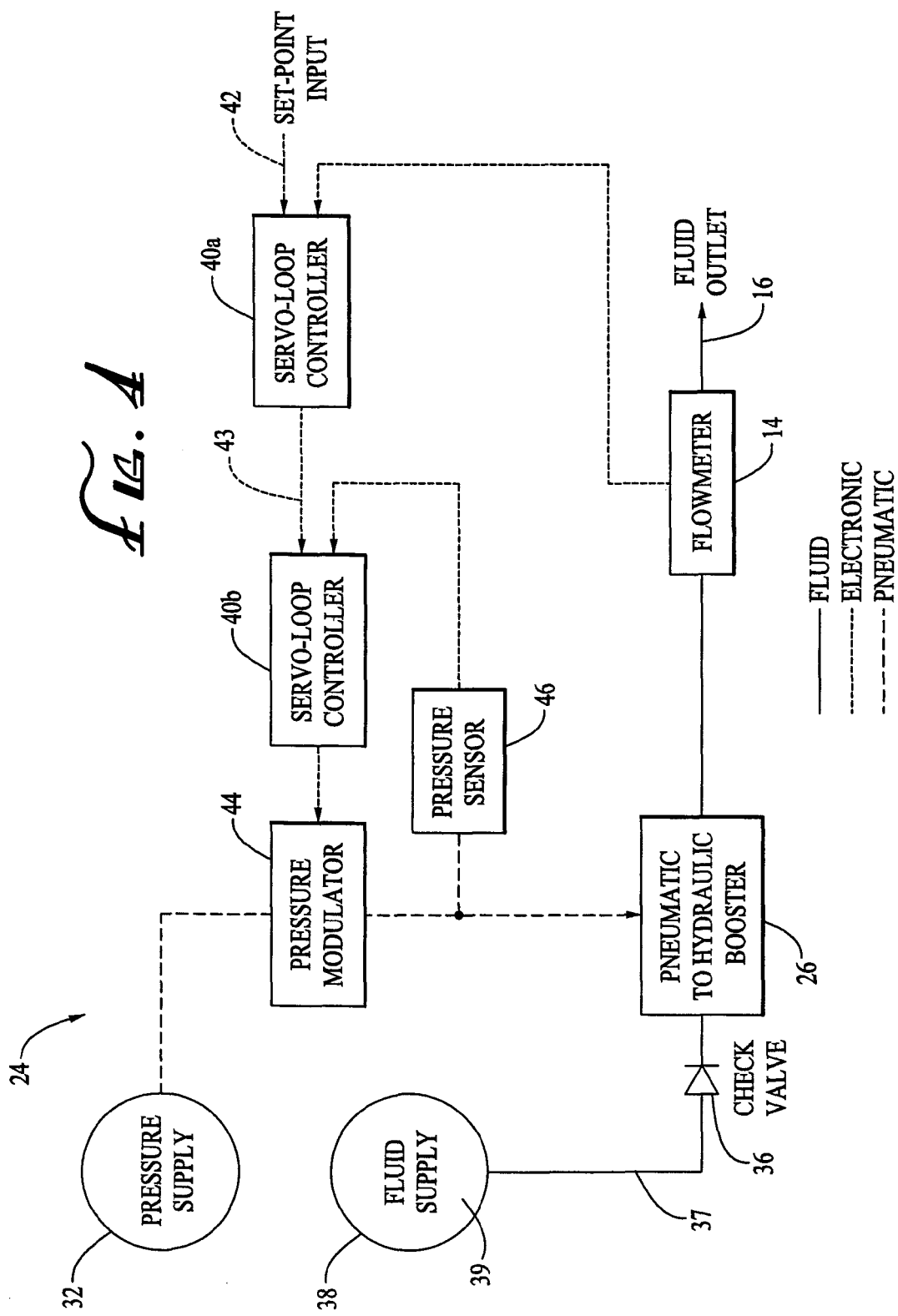

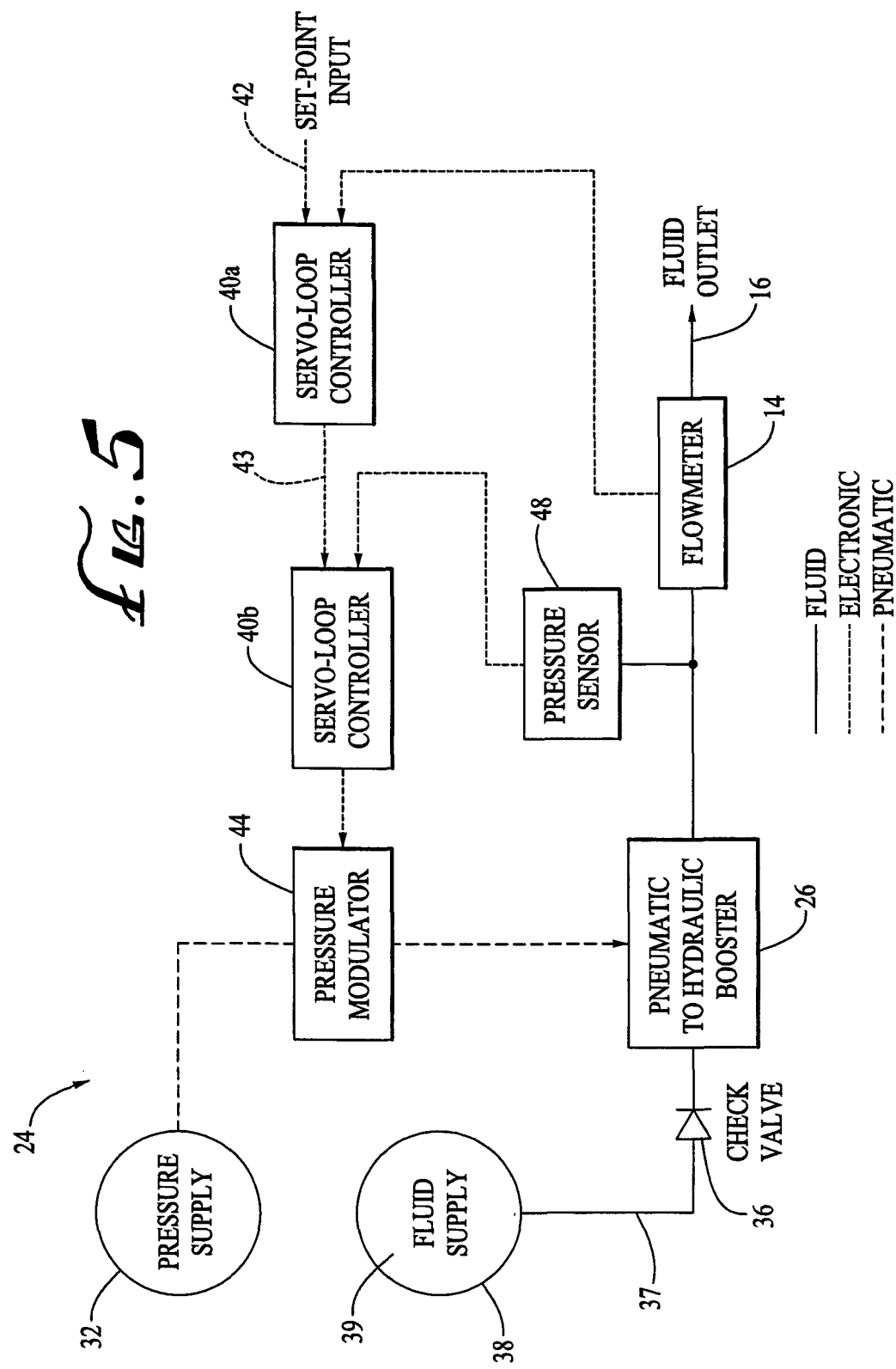

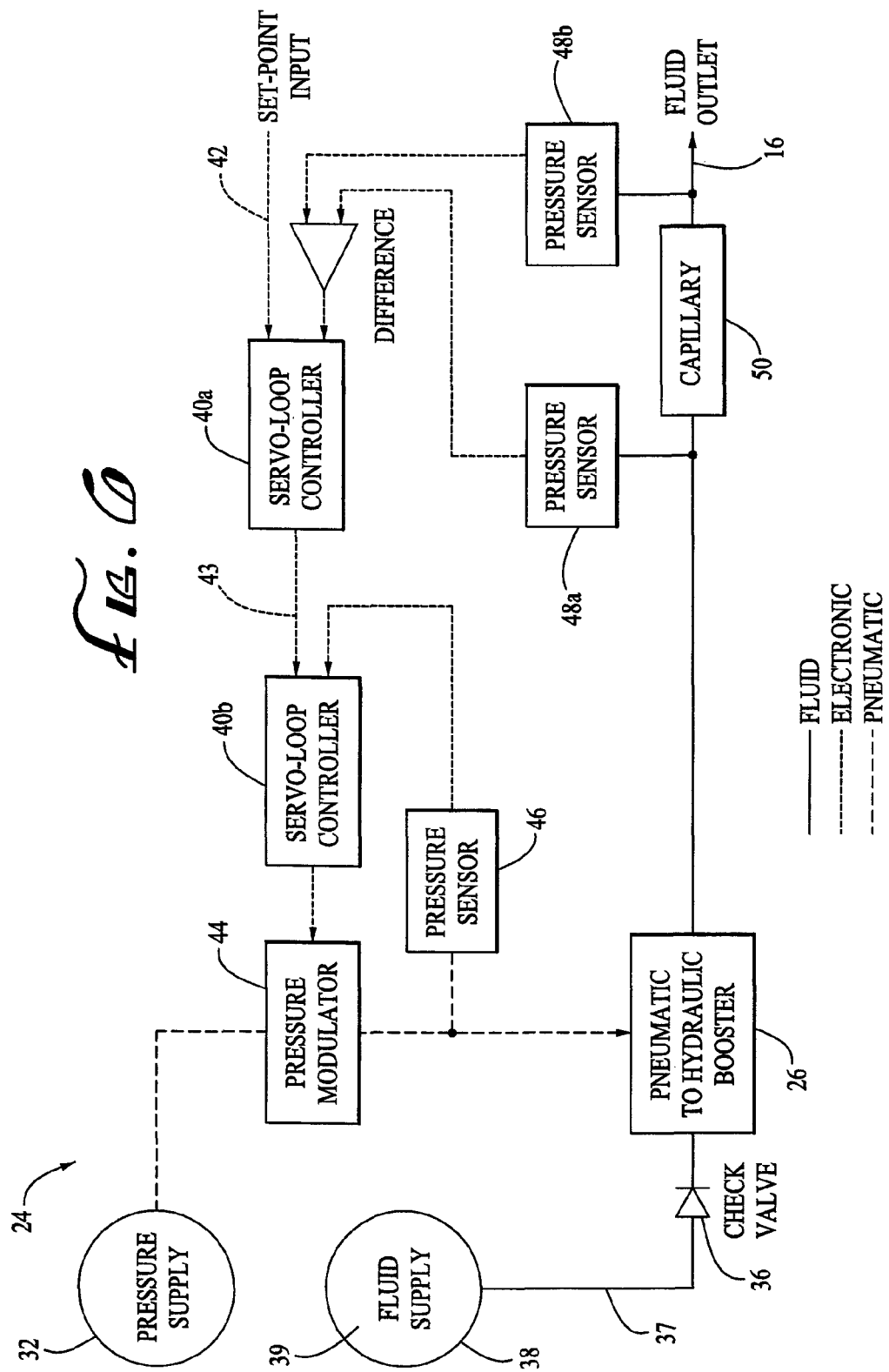

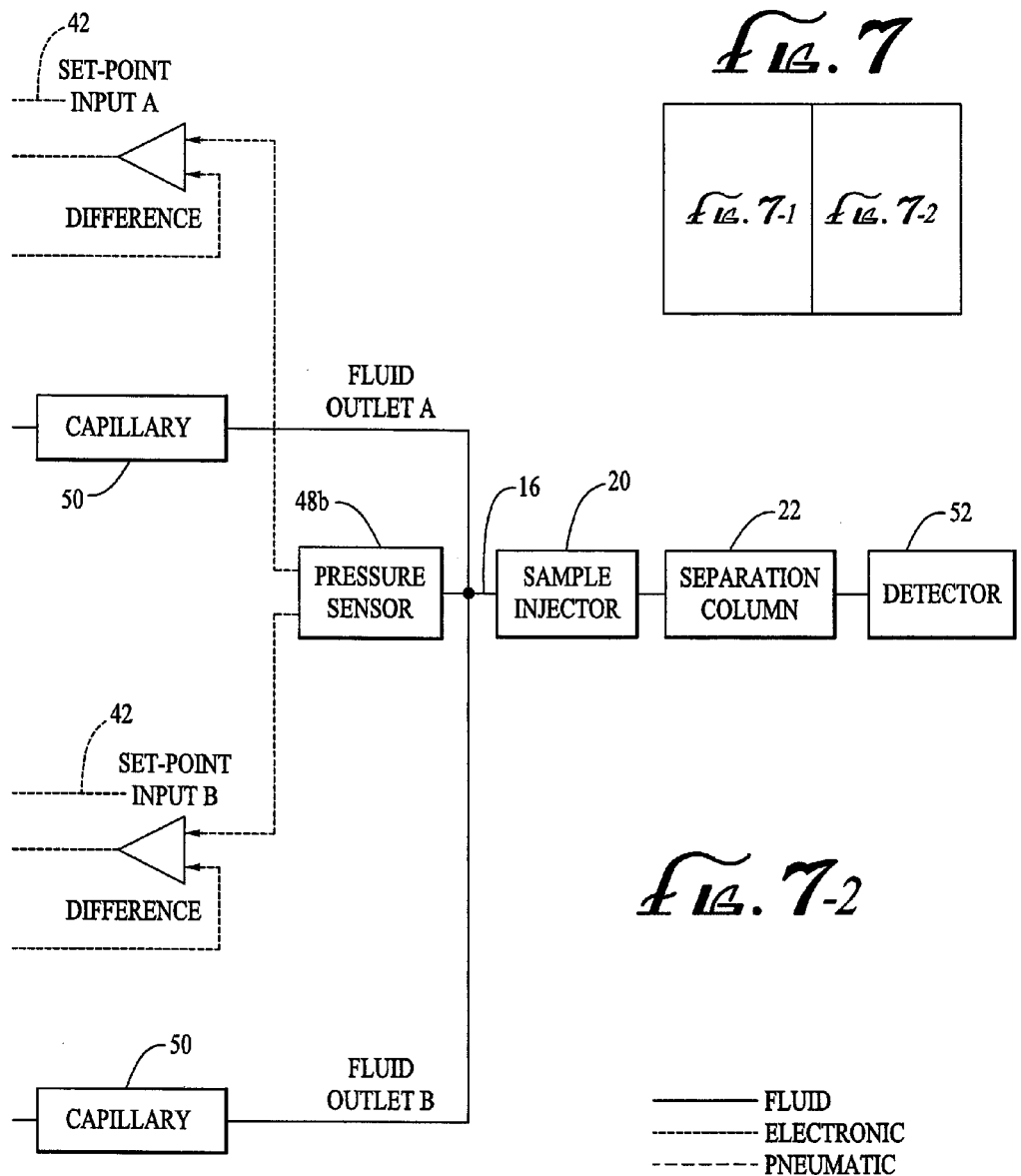

PRECISION FLOW CONTROL SYSTEM

CROSS REFERENCE TO RELATED APPLICATIONS

This application is a continuation application of the U.S. patent application Ser. No. 12/334,375 filed Dec. 12, 2008, now U.S. Pat. No. 7,927,477 which is a divisional of U.S. patent application Ser. No. 10/246,284, filed Sep. 17, 2002, now U.S. Pat. No. 7,465,382 that is related to U.S. patent application Ser. No. 10/155,474, filed May 24, 2002, that is a continuation-in-part of U.S. patent application Ser. No. 09/942,884 filed Aug. 29, 2001 that claims the benefit of U.S. Provisional application No. 60/298,147 filed Jun. 13, 2001, the entire disclosures of which are incorporated by reference in their entirety for any and all purposes.

BACKGROUND

The invention pertains to the field of precision fluid control for High Performance Liquid Chromatography ("HPLC") including gradient liquid chromatography ("LC"). Commercially available HPLC systems for carrying out analytical separations typically control fluid at flow rates of a few milliliters per minute ("ml/min") for columns of 4-5 mm in diameter. The current trend in LC is reducing the size and flow rates of the system in order to reduce the amount of waste generated, lower sample size requirements, and improve compatibility with robust detection systems such as mass spectrometers ("MS"). There is particular interest in columns with diameters in the range of 50 µm to 1 mm that are typically referred to as capillary columns. Since the flow rate of fluid in these capillary systems can range from nanoliters per minute ("nL/min") to 100 microliters per minute ("µl/min"), there is a need for precision flow control at low flow rates.

The precise control of flow rates is essential to analysis using HPLC. Uncontrolled variations in the flow rate and the fluid composition in HPLC systems produces a number of deleterious effects that compromise the utility and sensitivity of the method. Particularly, a known flow rate is required to reliably predict analyte retention times and thus reliably identify analytes. Also, temporal variations in flow rate, such as pulsations, can produce variations in detector signal that may be confused with the presence of an analyte, resulting in the identification of false analyte features. Temporal variations in flow rate may produce fluctuations in the detector baseline obscuring trace analyte signatures, degrading the minimum detectivity of the system.

The importance of flow control is even more critical for gradient separations where the fluid composition is varied during the course of the separation. In gradient HPLC, the fluid outputs from multiple pumps are summed to provide a desired flow rate of varying composition. Since the retention time of an analyte is very dependent on the time-varying composition of the eluting fluid, precise control of all fluids is critical.

Conventional HPLC pumping systems generally employ positive displacement methods, where the rate of mechanical displacement of a pump element, e.g. a lead-screw driven piston, provides a proportional rate of liquid flow. This method scales down poorly to low flow rates and is unable to control fluid flow with sufficient accuracy to generate reliable and rapid gradients for capillary HPLC systems. The origin of the low flow rate inaccuracies include: check valve leakage, pump seal leakage, flexing and creep of mechanical seals, thermal expansion of components and compression of the working fluid. Many of these issues can produce errors in flow rate larger than the flow rates desired in capillary chromatography. These systems also typically include pulse dampeners and/or fluid volumes to dampen fluctuations due to piston refilling. These volumes produce relatively high hydraulic capacitance in the system. This capacitance, in conjunction with the high hydraulic resistance of microbore columns, leads to slow time response.

The most common approach to achieve flow rates compatible with capillary HPLC is to split the pump output of conventional HPLC pumps. This method is described in Johannes P. C. Vissers, "Recent developments in microcolumn liquid chromatography" Journal of Chromatography A, vol 856 pp. 117-143 (1999); U.S. Pat. No. 6,402,946; and U.S. Pat. No. 6,289,914. In the flow splitting approach, some portion of the mixed solvent is split-off to provide the required flow rate to the column, the balance of the liquid is shunted to waste. The splitting element employs two different flow conductance paths to produce the two flow streams. The precision of this method is limited by changes that may occur in the relative hydraulic conductances of the two flow paths over time. Conductance changes, such as partial plugging of the chromatographic column, will result in changing the flow rate of fluid into the separation column. An additional problem with flow splitting is that it has proven difficult to remove delay times in gradients that result from dead volumes of the splitter based systems. Additionally, these systems generate large volumes of waste relative to the fluid that is actually used since the splitter discards the majority of the fluid in the system.

Agilent Technologies has recently attempted to address one of the problems of flowsplitters using a variable flow splitter with active feedback as disclosed at www.agilent.com. In this capillary HPLC system, high pressure fluids for the gradient separation are delivered by conventional positive displacement pumps and mixed at high volumetric flow rates (~1 ml/min). The flow rate of the mixture delivered to the column is directly measured and maintained by actively controlling a variable splitter valve. The system is still limited by the delay volumes (~5 µl) which effects chromatographic performance and the ability to accurately measure flow rates in a varying mixture. At flow rates typical for 300 and 100 µm diameter columns this introduces delay times of 1-10 minutes in the gradient. The delay times make flow rate measurements difficult since they depend on knowing the physical properties of the mixture in the flow sensor at a specific time. Despite the effort to carefully control flow rates, changes in the conductance of the capillary column can result in >20% errors in flow rate and take ~30 seconds for the system to respond to the conductance change.

In addition, there are several other HPLC systems that have active flow rate control. These systems were developed for high flow rate (>0.1 ml/minute) isocratic HPLC. An early system was developed by DuPont around 1970. The Dupont 833 precision Flow Controller worked together with the Dupont 830 liquid chromatograph (H. M. McNair and C. D. Chandler "High Pressure Liquid Chromatography Equipment—II", J. of Chrom. Sci., v12, pp 425-432 (1974)). The system worked by measuring the pressure drop across a flattened capillary downstream of the pump. The measured flow rate was used to modify the air pressure on a pneumatic piston. The system was designed to work with column diameters of 2.1 to 23.5 mm with high flow rates of up to 100 ml/min.

A gradient system which made use of flow rate feedback and pneumatic actuation was described by Tsukazaki in U.S. Pat. No. 5,777,213. This patent described the advantages for preparative liquid chromatography that typically operates at flow rates of 100's of ml/minute. This system makes use of direct pressurization of a liquid with air which was desirable for medicine or food processing. This method would be very undesirable for capillary HPLC where any bubbles that result from dissolved gasses will dramatically reduce system performance. Additionally, capillary HPLC is typically run at fairly high fluid pressures (greater than 1000 psi) which would make direct pneumatic control a safety concern.

An additional system, disclosed in Jacques C. LeBlanc, "The Stableflow Pump—a low-noise and drift-free pump for high performance liquid chromatography" Rev. Sci. Instrum., v62 pp 1642-1646 (1991), was developed for isocratic HPLC using flow rates between 0.1 and 100 ml/minute. This system measures the flow rate after exiting a column and detection cell. The flow rate was controlled by adjusting the temperature of a bath that contained a restricting capillary following the flowmeter. The desired flow rate was achieved using a feedback loop between the flow meter and the temperature bath.

While direct mixing of the fluids is the most robust and useful method for generating gradients, accomplishing this in low flow systems is clearly a challenge.

Accordingly, there is a need in the art for a precision flow control system that is capable of delivering fluid at low flow rates in the range of about 1 nanoliter/minute to about 100 microliters/minute and varying the flow rate in a prescribed manner that is both predictable and reproducible. In addition, it is desirable to have delay volumes of <1 µL and a response time of a few seconds or less.

SUMMARY

The present invention provides a precision flow control system that is capable of delivering fluid at low flow rates in the range of about 1 nanoliter/minute to about 100 microliters/minute and varying the flow rate in a prescribed manner that is both predictable and reproducible. Some embodiments have delay volumes <1 µL and response times of a few seconds or less.

A precision flow controller system according to the present invention comprises a plurality of fluid supplies in fluid communication with a fluid outlet so that a plurality of fluids mix before passing through the outlet; a pressure source for each fluid applying pressure to the respective fluid; a flowmeter for each fluid measuring the flow rate of the respective fluid; and a controller for each pressure source in communication with the respective flowmeter and the respective pressure source, wherein the controller compares the respective measured flow rate to a respective desired flow rate and adjusts the respective pressure source so that the respective fluid flows at the respective desired flow rate. Fluid can flow out of the fluid outlet at a flow rate of less than approximately 100 microliters/minute. The desired flow rates do not have to be the same for each fluid and can vary as a function of time so that the system is suitable to supply fluid to a separation column.

The flowmeters can be comprised of: a metering capillary having a sufficiently long length and sufficiently small inner diameter so that the pressure drop across the metering capillary is at least 5% of the input pressure to the metering capillary; and a pressure sensor for measuring the pressure drop across the metering capillary. The pressure drop can be at least 50 psi, for example. The capillary can have an inside diameter of less than approximately 50 microns.

The pressure source can be comprised of: electrokinetic pumps, electrokinetic flow controllers, mechanically activated pumps, and pneumatically activated pumps or any other variable pressure fluid supply known in the art.

For example, the pressure source can be comprised of: a pneumatic to hydraulic booster in operative fluid communication with the fluid supply; and a check valve between the fluid supply and the booster so that fluid flows unidirectionally from the fluid supply to the booster.

The controller can be comprised of: a pneumatic pressure supply in operative communication with the booster; and a pressure modulator located between the pneumatic pressure supply and the booster, wherein the pressure modulator controls the amount of pneumatic pressure supplied to the booster; and a servo-loop controller in communication with the respective flowmeter and the pressure modulator, wherein the servo-loop controller compares the measured flow rate to the respective desired flow rate and instructs the pressure modulator to adjust the pneumatic pressure supply so that the fluid flows at the desired flow rate.

The system preferably has a time response of less than one second so that when the measured flow rate does not equal the desired flow rate, the measured flow rate will equal the desired flow rate within one second.

In another embodiment, a low flow rate precision flow controller comprises: a fluid inlet; a fluid outlet in fluid communication with the fluid inlet; a pneumatic pressure supply; a pneumatic to hydraulic booster located between the fluid inlet and the fluid outlet and in operative communication with the pneumatic pressure supply, wherein the booster forces fluid out through the fluid outlet; a pressure modulator located between the pneumatic pressure supply and the booster, wherein the pressure modulator controls the amount of pneumatic pressure supplied to the booster; a flowmeter located between the booster and the fluid outlet wherein the flowmeter measures the flow rate of a fluid flowing from the booster to the fluid outlet; and a servo-loop in communication with the flowmeter and the pressure modulator, wherein the servo-loop compares the measured flow rate to a desired flow rate and instructs the pressure modulator to adjust the pneumatic pressure supply so that the fluid flows out of the fluid outlet at the desired flow rate, wherein the desired flow rate is less than approximately 100 micro liters/minute. The desired flow rate can also be less than 10 microliters/minute. A check valve can be located between the fluid inlet and the booster so that the fluid flows unidirectionally from the fluid inlet to the booster.

Preferably, the flow controller has a time response of less than one second so that when the measured flow rate does not substantially equal the desired flow rate, the measured flow rate will substantially equal the desired flow rate within one second. A method of mixing two fluids at low flow rates comprising the steps of: applying a pressure source to each fluid; measuring the flow rate of each fluid before mixing; sending a desired flow rate for each fluid to the controller; sending the measured flow rate for each fluid to the controller; and controlling the pressure source of each fluid with the controller so that the measured flow rates equal the respective desired flow rates. The desired flow rates do not have to be the same for each fluid and can vary as a function of time. The fluids can flow through a fluid outlet at a constant flow rate. The flow rate can be measured by a flowmeter comprising: a metering capillary having a sufficiently long length and a sufficiently small inner diameter so that the pressure drop across the metering capillary is at least 5% of the input pressure to the metering capillary at the desired flow rate; and a pressure sensor for measuring the pressure drop across the metering capillary. The method can have a time response of less than one second so that when the measured flow rate does not substantially equal the desired flow rate, the measured flow rate will substantially equal the desired flow rate within one second.

BRIEF DESCRIPTION OF THE DRAWINGS

These and other features, aspects and advantages of the present invention will become better understood with regard to the following description, appended claims, and accompanying drawings where:

FIG. 2 schematically illustrates the system of FIG. 1 having an injection valve and a separation column attached to the fluid outlet.

FIG. 3 schematically illustrates a precision flow controller that can make up part of the system of FIG. 1.

FIG. 4 schematically illustrates a second embodiment of a precision flow controller that can make up part of the system of FIG. 1.

FIG. 5 schematically illustrates a third embodiment of a precision flow controller that can make up part of the system of FIG. 1.

FIG. 6 schematically illustrates a fourth embodiment of a precision flow controller that can make up part of the system of FIG. 1.

DESCRIPTION

The present invention is directed to a flow controller capable of providing a low and controlled flow rate of a liquid. Here 'low' means in the range of about 1 nanoliter per minute to about 100 microliters per minute. Here 'controlled' means the capacity to vary the flow rate in some prescribed manner that is both predictable and reproducible.

Figure 1:
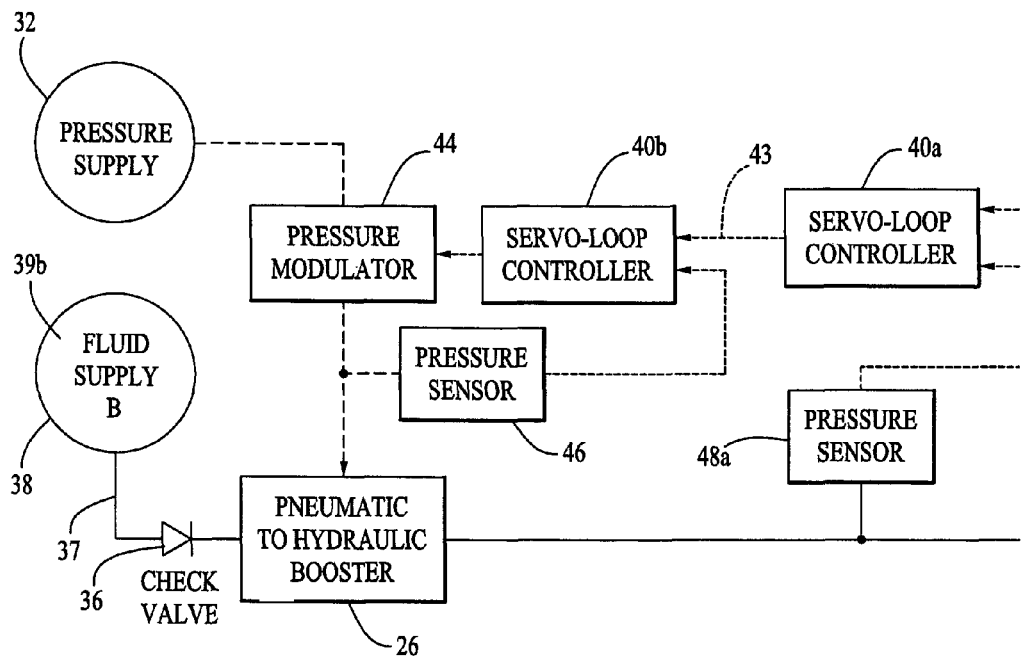
FIG. 1 schematically illustrates a precision flow controller system in accordance with the present invention.

A schematic of a basic flow controller system 10 for two fluids is shown in FIG. 1. It includes two variable pressure fluid supplies 12, a flowmeter 14 for each fluid 39, and a single fluid outlet 16. A signal from each flowmeter is sent to a controller 18, which in turn adjusts the pressure of the fluid supplies 12 so that the fluid 39 flows out of the fluid outlet 16 at a desired flow rate. The desired flow rate can be less than 100 microliters/minute or less than 10 microliters/minute, for example.

The fluids 39 are mixed after exiting the flowmeters 14 and before passing through the fluid outlet 16. Mixing can occur via diffusion or via passive or active devices. Ideally, the mixed fluids only need to flow through a minimal volume, 100 nL for example, to the fluid outlet 16, the delay volume, so that changes in mixture composition are accurately represented, with little time delay, in the fluid exiting through the fluid outlet.

Preferably, the controller 18 can adjust flow rates of the fluids 39 to compensate for volumetric changes of the mixture that will affect the flow rate of the mixture. Hence, preferably, the controllers 18 can obtain the physical properties of the fluid upon which the volume depends, such as composition, temperature and pressure. For example, the composition and mixing ratio of both fluids can be input to the controller; the flowmeter can measure the pressure; and a thermocouple in communication with the controller can take the temperature measurement. Alternatively, the system can be temperature controlled and the temperature communicated to the controller.

The flowmeter 14 may be of any type known in the arts including but not limited to: determining flow rate from measured pressure difference across a known flow conductance; a Coriolis flowmeter as disclosed in P. Enoksson, G. Stemme and E. Stemme, "A silicon resonant sensor structure for Coriolis mass flow measurements," J. MEMS vol. 6 pp. 119-125 (1997); a thermal mass-flowmeter; a thermal heat tracer as disclosed in U.S. Pat. No. 6,386,050; and an optical flowmeter, for example, a Sagnac interferometer as disclosed in R. T. de Carvalho and J. Blake, "Slow-flow measurements and fluid dynamics analysis using the Fresnel drag effect, Appl. Opt. vol. 33, pp. 6073-6077 (1994). Preferably the flowmeter 14 provides accurate and precise measurements of flow rates in the range of 100 µL/min to 10 nL/min. It is further preferable that the flowmeter 14 provide a signal that is continuous over all desired flow rates including fluid flow in both directions. It is further preferable that the signal bandwidth of the flowmeter 14, i.e. the frequency corresponding to the minimum time between meaningful readings, is faster than one Hertz, and more preferable faster than 10 Hertz.

These objectives can be accomplished by a flowmeter comprising a metering capillary having a sufficiently long length and a sufficiently small inner diameter so that the pressure drop across the metering capillary is at least 5% of the input pressure to the capillary at the desired flow rate and a pressure sensors for measuring the pressure drop across the metering capillary, wherein the input pressure is the pressure of the fluid as it enters the capillary. One or more pressure sensors can be used to measure the pressure drop across the capillary directly or by measuring the pressure at both ends of the capillary and subtracting one pressure measurement from the other. The pressure sensor can be a pressure transducer. Minimizing the volume and size of the pressure transducers to 5 microliters, for example, allows for rapid response of the flowmeter since the compressibility of the fluid and the deflection of the pressure transducer membrane contribute to the time response.

For example, a pressure drop of about 450 psi through a 10 cm long and 10 micron ID capillary indicates a flow rate of about 500 nL/min for water at room temperature. Similar relations can be determined for other fluids, geometries, pressure differences, and lengths of tubing using the well known Darcy's law for pressure driven flow. Accurate flow rate measurements will also require knowledge of the fluid viscosity.

The variable pressure fluid supplies 12 need not be the same and can be of any type known in the arts or developed in the future including but not limited to: direct electrokinetic pumps, such as those disclosed in U.S. Pat. No. 5,942,093, which is incorporated herein by reference; electrokinetic flow controllers, such as those disclosed in U.S. patent application Ser. Nos. 09/942,884 and 10/155,474; electropneumatic pumps with and without hydraulic amplifiers, such as those described later in this application; and mechanically actuated pumps. Although many current designs of positive displacement pumps, such as lead-screw driven pumps, do not have the performance to address the precision at the low flow rate ranges, they may be used in active flow rate feedback in future designs. Preferably the variable pressure fluid supplies 12 are continuously variable, can provide flow rates in the range of 1 nL/minute to 100 µL/minute into back pressures of up to 5000 psi or higher, and have a response time of seconds or less, thus allowing rapid changes in flow rates.

Because the flow rate is measured and the measured flow rate is used to adjust the variable pressure fluid supply as opposed to adjusting the mechanical displacement of a pump element, e.g., a lead-screw driven piston, so that it is proportional to a desired flow rate, the system is capable of delivering fluid predictably and reproducibly at low flow rates even if there is check valve leakage, pump seal leakage, flexing and creep of mechanical seals, thermal expansion of components and compression of the working fluid.

Preferably the system has a response time of less than one second so that when the measured flow rate does not substantially equal the desired flow rate, the measured flow rate will substantially equal the desired flow rate within one second, wherein substantially equal means within 5%.

The unique combination of a variable pressure supply with fast time response and the low volume, capillary-based flow meter described previously provides a low flow rate flow controller with excellent time response. The time response of the system can be understood in terms of the hydraulic resistances and capacitances. As with an electronic circuit, the product of these two gives a characteristic time constant. The hydraulic capacitance in the disclosed systems is dominated by the volumes and compressibility of the fluid, but also includes contributions from sources such as the deflection of the diaphragm in the pressure transducer.

The capillary flow meter described previously has a reasonably high hydraulic resistance, but a very low fluid volume, allowing rapid response. The compressible liquid volume (leading to capacitance) in the illustrated embodiments is on the order of 5 microliters and is due to the pressure transducer mounting.

For fast flow rate changes in the overall flow controller, the variable pressure source preferably has a rapid time response (i.e., a small time constant). In the case of an electrokinetic pump or electrokinetic flow controller, the hydraulic resistance may be high, but the compressible volume is very low which allows designs with very small time constants. The pneumatic booster pressure supplies later described have larger fluid volumes but the pistons have very low resistance to volumetric changes—once again allowing very rapid time response.

The combined fluids 39 can be directed to an injection valve 20 and an HPLC separation column 22 as shown in FIG. 2. When this is the case, preferably, the mixture is formed at high pressure and just prior to introduction to the column 22 thus minimizing the delay volume. Alternatively, or in addition, the combined fluids can be directed to any other components known in the HPLC arts, such as a detector.

A flow controller 24, which comprises the variable pressure fluid supply 12, the flowmeter 14, and the controller 18 of the flow controller system 10 of FIG. 1, is illustrated in greater detail in FIG. 3. A pneumatic-to-hydraulic booster 26 employs two coupled pistons 28 and 30. A pneumatic pressure supply 32 is coupled to a first piston 28. The resulting force translates to the fluid 39 in a cylinder 34 on the opposite side of a second piston 30. The gain of the booster 32 is proportional to the ratio of the first piston area to the second piston area. This ratio is typically greater than one, but may also be equal to one (direct transfer of pressure with no amplification) or less than one for lower pressure applications. Thus, the fluid pressure is controlled by varying the pneumatic pressure applied to the first piston 28. Once the fluid 39 in the cylinder 34 is expended, the cylinder is refilled by withdrawing the second piston 30 and pulling fresh fluid from a fluid supply 38 through a fluid inlet 37 and a check valve 36 into the cylinder 34.

The flow rate as measured by the flowmeter 14 is input to a servo-loop controller 40. A desired flow rate is input to the servo-loop controller 40 through a set-point input 42. The servo-loop controller 40 then compares the measured flow rate to the desired flow rate and then, if the measured flow rate does not equal the desired flow rate, instructs a pressure modulator 44 to adjust the pneumatic pressure to the first piston 28 of the booster 26 to achieve the desired liquid flow rate. The desired flow rate can be less than 100 microliters/minute or less than 10 microliters/minute, for example.

The fluid source 38, the check valve 36 and the pneumatic to hydraulic booster 26 can make up one of the variable pressure fluid supplies 12 of FIG. 1. The pneumatic pressure supply 32, the pressure modulator 44, the servo-loop controller 40 and set-point input 42 can make up the controller 18 of FIG. 1. The flow controller 24 preferably has a time response of less than one second so that when the measured flow rate does not equal the desired flow rate, the measured flow rate equals the desired flow rate within one second.

The pneumatic-to-hydraulic booster 26 can be of any type known in the arts, including but not limited to a liquid head that uses a dynamic seal on a moving solid rod that displaces liquid, where the rod is coupled to the shaft of a common pneumatic piston.

The pressure modulator 44 can be any of the means known in the art of pneumatic control including but not limited to an electro-pneumatic controller. Typically in electro-pneumatic controllers, an input current or voltage produces a command signal to one or more actuators within the electro-pneumatic controller. This actuator generally acts to increase or decrease the amount of airflow through the electro-pneumatic controller in order to maintain an output pressure proportional to the command signal.

The servo-loop controller 40 can be any type known in the art for example, a PID loop, and can be constructed using discrete analog circuits, discrete digital circuits, dedicated microprocessors or a computer, for example.

FIG. 4 shows a variation on the flow controller 24 illustrated in FIG. 3 that employs two nested servo loops. An outer servo-loop 40a compares the measured flow rate to the desired flow rate then outputs a pressure setpoint 43 to an inner servo-loop 40b. A gas pressure sensor 46 measures the pneumatic pressure applied to the first piston 28 of the booster 26. The measured pneumatic pressure is input to the inner servo-loop 40b controller as well as the pressure setpoint 43 from the outer servo-loop controller 40a. If necessary to achieve the desired flow rate, the inner servo-loop 40b instructs the pressure modulator 44 to adjust the pneumatic pressure applied to the first piston 28 of the booster 26.

FIG. 5 shows a variant of the flow controller of FIG. 4 wherein one of the inner servo-loop 40b inputs is the measured fluid pressure from a fluid pressure sensor 48 located between the booster 26 and the flowmeter 14.

FIG. 6 shows another variant of the device in FIG. 4 wherein the flowmeter 14 comprises a length of capillary tubing 50 having a small diameter and a first and a second pressure sensor 48a and 48b, respectively, one located on either end of the tubing. The flow rate is calculated using the measured pressure difference across the known flow conductance of the tubing 50.

The embodiment illustrated in FIG. 6 uses the same inner servo-loop 40b as the embodiment illustrated in FIG. 4. Alternatively, the first pressure sensor 48a of the flowmeter 14 can provide input to the inner servo-loop 40b.

Figure 7:
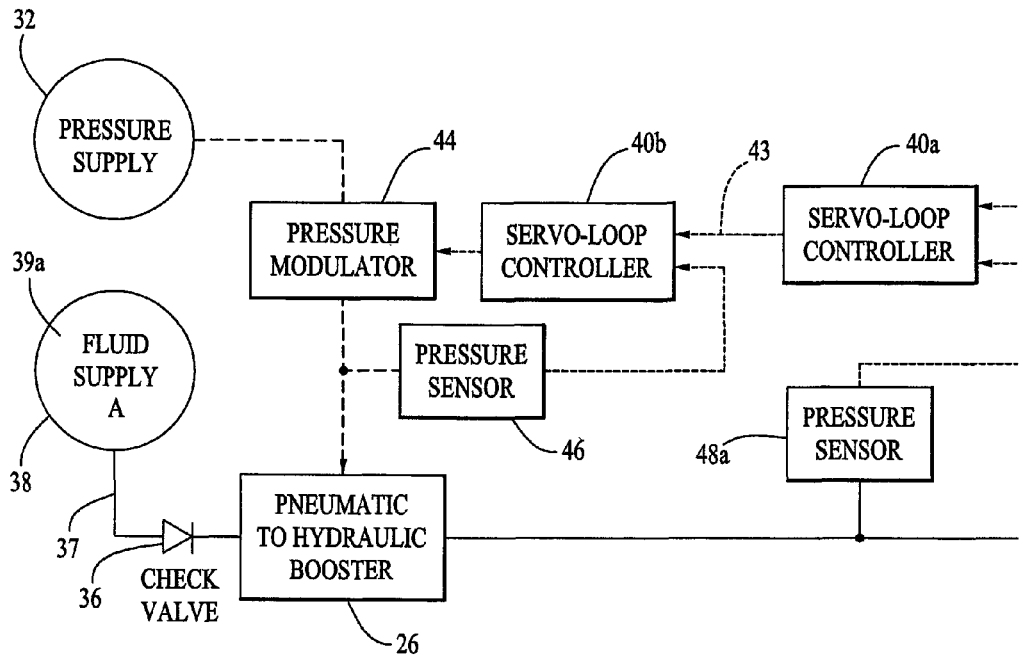
FIG. 7 is a detailed illustration of one possible embodiment of the system illustrated in FIG. 2.

One possible embodiment of the flow controller system 10 illustrated in FIG. 2 is shown in detail in FIG. 7. The embodiment has two of the flow controllers 24 illustrated in FIG. 6, with both flow controllers sharing the second pressure sensor 48b. Additionally, the separation column 22 leads to a detector 52. In some cases, additional separation columns or other fluidic devices could be inserted after the first separation column 22.

The detector 52 can be any of those known in the HPLC arts, such as: a laser-induced fluorescence detector, an optical absorption detector, a refractive index or electrochemical detector, a mass spectrometer, or NMR spectrometer.

This embodiment can provide a predetermined flow rate of a mixed fluid to the separation column 22 while providing a programmed variation in fluid composition. The flow rates of a first fluid 39a and a second fluid 39b from their respective sources 38 can be independently measured and servo-controlled to meter the independent flows proportional to the respective set-point inputs. The programmed variation in fluid composition can be in the form of a series of step changes, a continuous ramp, i.e. a gradient, or any of the other forms known in the separation arts. In other embodiments, attendant flow controllers and servo loops can be combined to provide for more complicated or broad ranging fluid composition variations.

Thus, two or more flow controllers 24 can be combined to deliver fast, accurate, and reproducible gradients for use in microscale separations that require extremely low flow rates. In this system, all of the flow goes directly into the separation column 22 and no excess fluid is shunted to waste as is commonly employed in systems with flow splitting. Additionally, the attainable low flow rates enable the system to supply an eluant directly into a mass spectrometer. Flow controllers embodying the invention can also be run in parallel from common sources of fluids to perform multiple separations in parallel.

Embodiments of the invention provide a liquid flow rate that is relatively free of pressure pulsations. Embodiments of the invention can be configured to provide a controlled flow rate of liquid at pressure ranging from about one atmosphere to over 10,000 psi. Applications include but are not limited to: gradient HPLC, fluid delivery to a mass spectrometer, flow injection analysis, drug delivery, and supply of liquid reactants to a chemical reactor.

EXAMPLES

Figure 8:
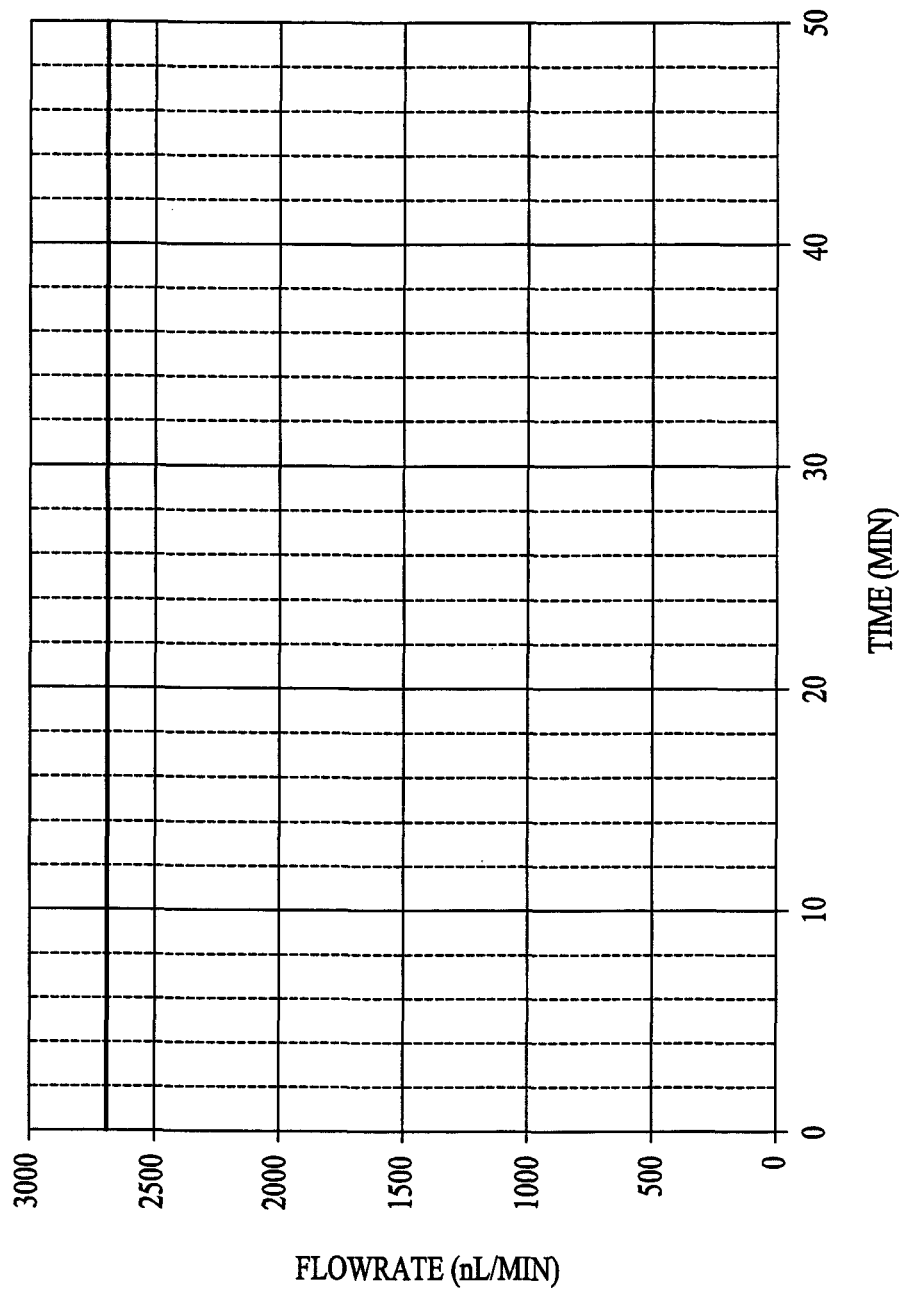
FIG. 8 is a graph showing the flow rate of a fluid in the controller of FIG. 6.

FIG. 8 shows the measured flow rate from the system described in FIG. 6, where the setpoint was set to a constant value of 2700 nL/min over 50 minutes. In this system, the pressure modulator 44 was an electro-pneumatic controller ControlAir 900-EHD, the pneumatic-to-hydraulic booster 26 was Haskel MS-36, and the pump fluid was deionized water. The pressure sensors 48a and 48b were two Entran EPX transducers. The transducers were on either side of a 10 cm length of a 10 µm ID capillary tube 50. The pressure drop across the capillary tube was about 100 psi. The flow rate was calculated by a microprocessor. The resulting metered flow of liquid was accurate within 0.02% of its setpoint over the duration of the test, or a flow rate accuracy of 0.56 nL/min RMS.

Figure 9:
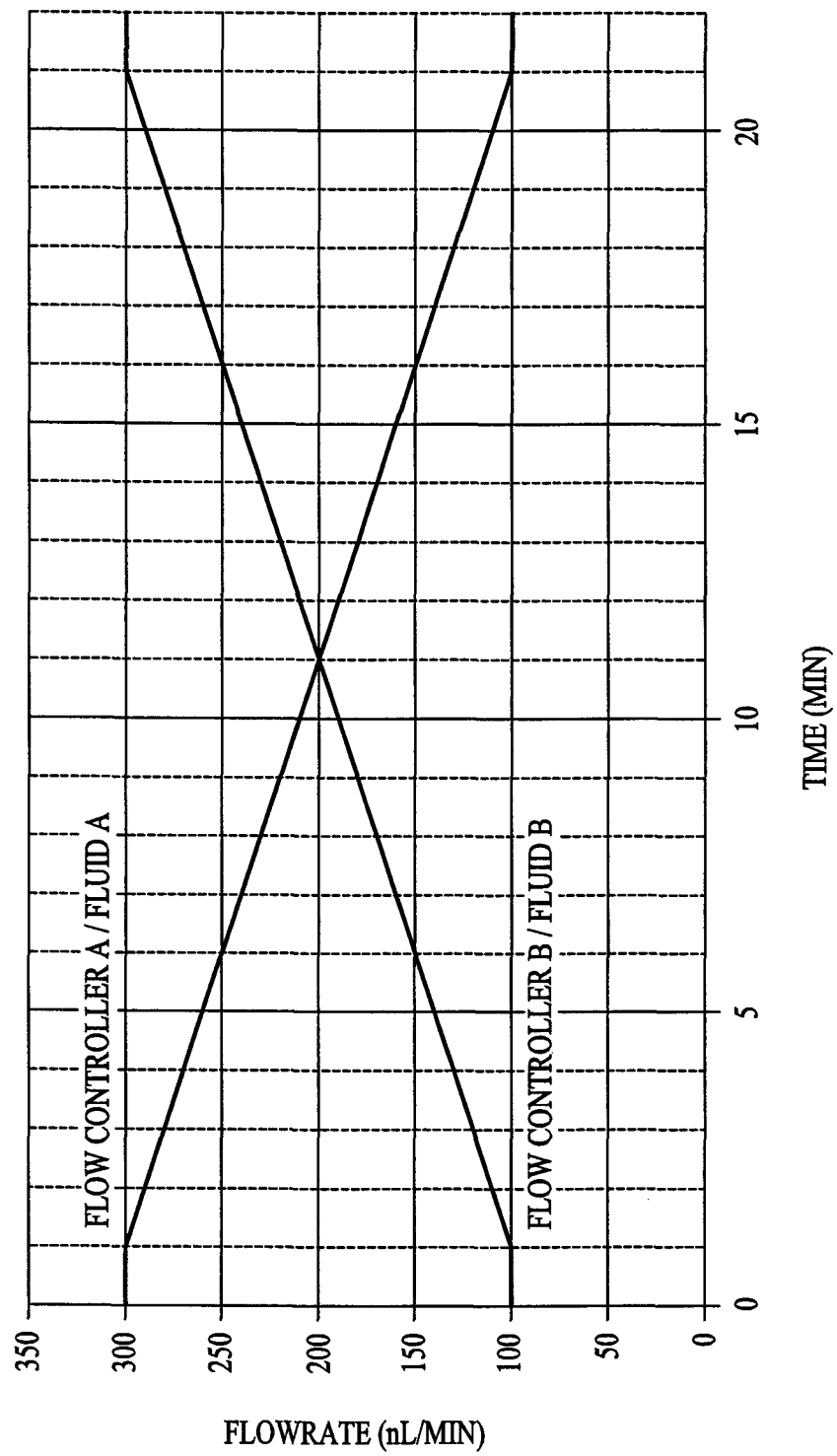
FIG. 9 is a graph showing the flow rates of two fluids in the system of FIG. 7.

The data shown in FIG. 9 were generated using the system shown in FIG. 7. The flow profile was a 20 minute gradient delivery of the first and second fluids, 39a and 39b, respectively, water and acetonitrile, respectively, with a one minute period of constant flow at the beginning and end of the test. Each flow controller was programmed to vary its flow rate over a range of 300 to 100 nL/min. The two streams of fluid were mixed in concentrations ranging from 25% to 75% over the duration of the test. The mixture ratio varied linearly over time so that the summed flows were maintained at a constant flow rate of 400 nL/min into the column. The measured flow rate from each controller indicates accuracy within 0.28 nL/min RMS of the setpoint over the full range of the test conditions.

Figure 10:
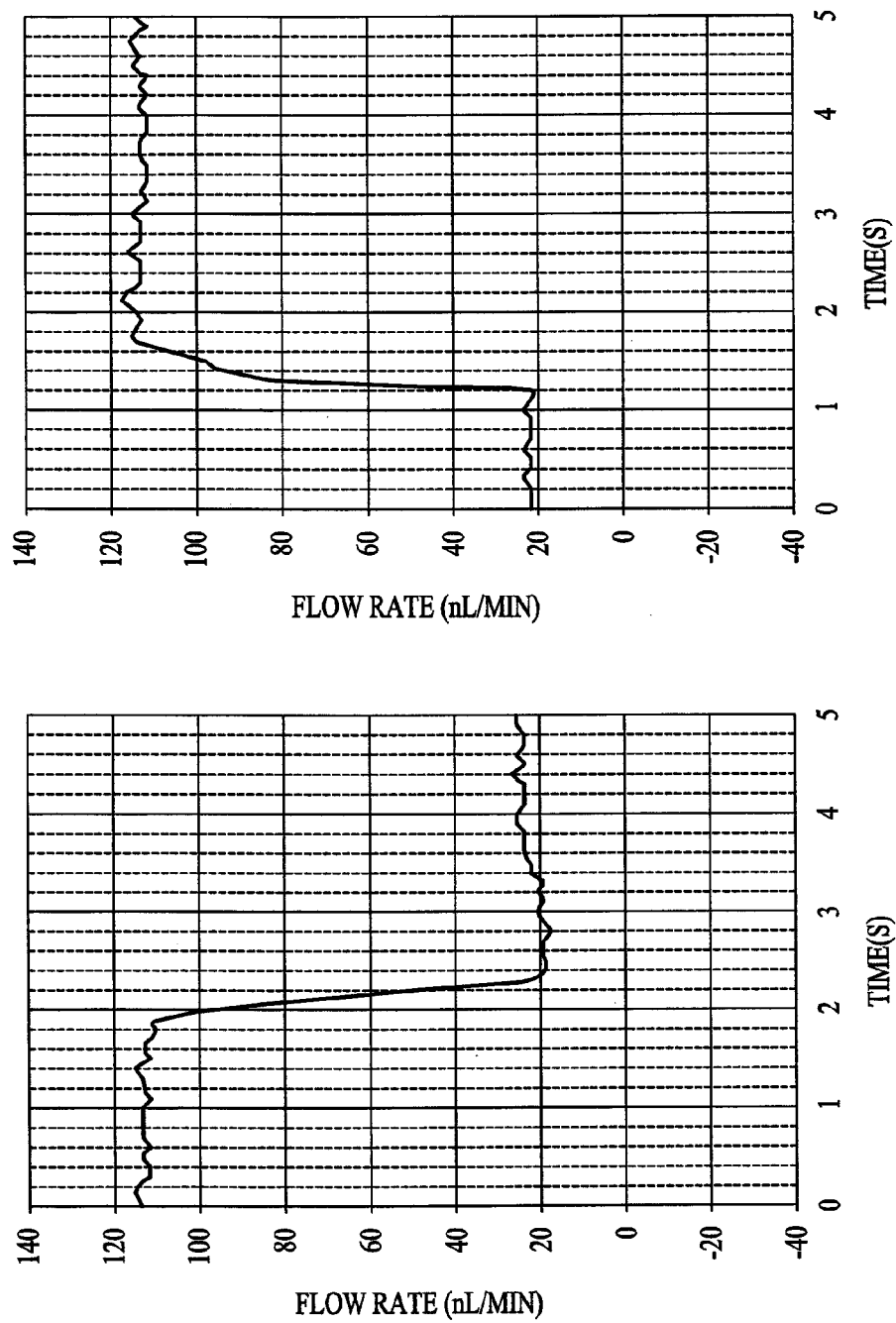
FIG. 10 is a graph showing the response time of a pressure modulator of FIG. 7.

FIG. 10 shows the response time of the pressure modulators of FIG. 7. The response time is demonstrated to be less than one second so that when the desired flow rate does not equal the measured flow rate, the measured flow rate will equal the desired flow rate within one second. Fast response changes in flow rate, as illustrated in FIG. 10, can be used in a number of analytical methods to conduct stopped flow or peak-parking to increase integration time and improve detection sensitivity.

Although the present invention has been described in considerable detail with reference to certain preferred versions thereof, other versions are possible. For example, three or more flow controllers can be used in a single flow controller system. Therefore, the spirit and scope of the appended claims should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" for "step" clause as specified in 35 U.S.C. §112.

What is claimed is:

1. A low flow rate precision flow controller system comprising:
   (a) a plurality of continuously variable pressure fluid supplies delivering a plurality of fluids;
   (b) a single fluid outlet being in fluid communication with the plurality of fluid supplies, the plurality of fluids being mixed before exiting through the outlet;
   (c) a plurality of pressure sources corresponding to the plurality of fluids, each pressure source applying pressure to each fluid;
   (d) a plurality of capillary tube thermal mass flowmeters, each flowmeter detecting the flow rate of each fluid of the corresponding plurality of fluids; and
   (e) a controller for electronic flow control in communication with the respective flowmeter and the respective pressure source, wherein the controller compares the respective measured flow rate to a respective desired flow rate and adjusts the respective pressure source so that the respective fluid flows at the respective desired flow rate, wherein the fluids flow out of the fluid outlet at a flow rate of less than approximately 100 microliters/minute.

2. The system of claim 1, wherein the desired flow rates are different in values for each fluid.

3. The system of claim 1, wherein the desired flow rates are less than 10 microliters/minute.

4. The system of claim 1, wherein the desired flow rates of the fluids vary as a function of time.

5. The system of claim 1, wherein the mixed fluids flow through the fluid outlet at a substantially constant flow rate.

6. The system of claim 1, further comprising a separation column in fluid communication with the fluid outlet.

7. The system of claim 6, further comprising a detector in fluid communication with an outlet end of the separation column.

8. The system of claim 1, wherein each flowmeter comprises a metering capillary having an inside diameter of less than 50 microns.

9. The system of claim 1, wherein the mixed fluid exiting the flowmeter flows through a minimal volume of 100 nL before exiting the fluid outlet.

10. The system of claim 1, wherein the pressure sources are mechanical pumps.

11. The system of claim 1, wherein at least one pressure source comprises an electrokinetic pump.

12. The system of claim 1, wherein at least one pressure source comprises an electrokinetic flow controller.

13. The system of claim 1, wherein at least one pressure source comprises a pneumatically activated pump.

14. The system of claim 1, wherein at least one pressure source comprises a mechanically activated pump.

15. The system of claim 1, wherein the system has a time response of less than one second so that when the measured flow rate does not substantially equal the desired flow rate, the measured flow rate will substantially equal the desired flow rate within one second.

16. A low flow rate precision flow controller system comprising:
  (a) a plurality of fluid supplies in fluid communication with a fluid outlet so that a plurality of fluids mix before flowing through the outlet;
  (b) a mechanical pump for each fluid applying pressure to the respective fluid;
  (c) a capillary-tube thermal mass flowmeter for each fluid for measuring the flow rate of the respective fluids;
  (d) a thermocouple in communication with the capillary-tube thermal mass flowmeter for taking a temperature measurement; and
  (e) at least one controller for each mechanical pump in communication with the respective flowmeter via respective thermocouple and the respective pressure source, wherein the at least one controller compares the respective measured flow rate to a respective desired flow rate and adjusts the respective mechanical pump so that the respective fluid flows at the respective desired flow rate, wherein the fluids flow out of the fluid outlet at a flow rate of less than approximately 100 microliters/minute.

* * * * *